United States Patent
Van Valen et al.

(10) Patent No.: US 9,060,845 B2
(45) Date of Patent: Jun. 23, 2015

(54) SYSTEMS AND METHODS FOR DISRUPTION OF AN EYE LENS

(71) Applicant: Biolase, Inc., Irvine, CA (US)

(72) Inventors: Marcia Van Valen, Aliso Viejo, CA (US); William E. Brown, Jr., Roswell, GA (US); Daniel Durrie, Mission Hills, KS (US)

(73) Assignee: Biolase, Inc., Irvine, CA (US)

( * ) Notice: Subject to any disclaimer, the term of this patent is extended or adjusted under 35 U.S.C. 154(b) by 0 days.

(21) Appl. No.: 13/633,505

(22) Filed: Oct. 2, 2012

(65) Prior Publication Data

US 2013/0085482 A1     Apr. 4, 2013

Related U.S. Application Data

(60) Provisional application No. 61/542,702, filed on Oct. 3, 2011, provisional application No. 61/551,826, filed on Oct. 26, 2011.

(51) Int. Cl.
| | |
|---|---|
| *A61B 18/18* | (2006.01) |
| *A61F 9/008* | (2006.01) |
| *A61N 5/06* | (2006.01) |
| *A61B 19/00* | (2006.01) |

(52) U.S. Cl.
CPC ........ *A61F 9/008* (2013.01); *A61F 2009/00889* (2013.01); *A61F 2009/00872* (2013.01); *A61F 9/00804* (2013.01); *A61F 9/00821* (2013.01); *A61N 5/062* (2013.01); *A61F 9/00802* (2013.01); *A61F 9/00825* (2013.01); *A61B 19/5202* (2013.01); *A61F 2009/0087* (2013.01); *A61F 2009/00887* (2013.01)

(58) Field of Classification Search
CPC ............ A61F 2009/00887; A61F 2009/00889; A61F 9/008; A61F 2009/00872; A61F 9/00804; A61F 2009/0087; A61F 9/00821
USPC ...................................... 606/4, 5, 6
See application file for complete search history.

(56) References Cited

U.S. PATENT DOCUMENTS

| | | | |
|---|---|---|---|
| 5,222,952 | A | 6/1993 | Loertscher |
| 5,439,462 | A * | 8/1995 | Bille et al. .................. 606/6 |
| 5,549,598 | A | 8/1996 | O'Donnell, Jr. |
| 5,643,250 | A | 7/1997 | O'Donnell |
| 5,919,186 | A | 7/1999 | Bath |
| 6,142,990 | A | 11/2000 | Burk |
| 6,389,193 | B1 | 5/2002 | Kimmel et al. |
| 6,567,582 | B1 | 5/2003 | Rizoiu et al. |

(Continued)

OTHER PUBLICATIONS

International Search Report and Written Opinion received in corresponding/related PCT Patent Application No. PCT/US12/58455, filed Oct. 2, 2012. Mailing Date of Search Report and Written Opinion: Dec. 24, 2012.

(Continued)

*Primary Examiner* — Lynsey Crandall
*Assistant Examiner* — Sebastien X Lukjan
(74) *Attorney, Agent, or Firm* — Greenberg Traurig, LLP

(57) ABSTRACT

Systems and methods are provided for ablating a lens of an eye. An access incision is made through outer eye tissue to access the lens. A laser tool is inserted through the access incision. Electromagnetic energy is focused using the inserted laser tool to ablate a portion of the lens, where said ablation breaks the lens into a plurality of pieces for removal from the eye.

20 Claims, 13 Drawing Sheets

(56) References Cited

U.S. PATENT DOCUMENTS

| | | |
|---|---|---|
| 6,623,477 B1 | 9/2003 | Elbrecht et al. |
| 6,743,221 B1 | 6/2004 | Hobart et al. |
| 7,384,419 B2 | 6/2008 | Jones et al. |
| 7,402,158 B2 * | 7/2008 | Scheller et al. .................. 606/4 |
| 7,421,186 B2 | 9/2008 | Boutoussov et al. |
| 7,620,290 B2 | 11/2009 | Rizoiu et al. |
| 7,665,467 B2 | 2/2010 | Jones et al. |
| 7,751,895 B2 | 7/2010 | Jones et al. |
| 7,785,321 B2 | 8/2010 | Baerveldt et al. |
| 7,878,204 B2 | 2/2011 | Van Valen et al. |
| 8,241,035 B2 | 8/2012 | Jones et al. |
| 2003/0093149 A1 | 5/2003 | Glazier |
| 2006/0195076 A1 | 8/2006 | Blumenkranz et al. |
| 2006/0216329 A1 | 9/2006 | Peyman |
| 2006/0271025 A1 | 11/2006 | Jones et al. |
| 2007/0042315 A1 | 2/2007 | Boutoussov et al. |
| 2007/0043340 A1 | 2/2007 | Thyzel |
| 2008/0033407 A1 | 2/2008 | Jones et al. |
| 2008/0097416 A1 * | 4/2008 | Jones et al. ....................... 606/4 |
| 2008/0161781 A1 * | 7/2008 | McArdle et al. .................. 606/6 |
| 2008/0269731 A1 | 10/2008 | Swinger et al. |
| 2009/0062779 A1 | 3/2009 | Rizoiu et al. |
| 2009/0298004 A1 | 12/2009 | Rizoiu et al. |
| 2010/0042082 A1 | 2/2010 | Rizoiu et al. |
| 2011/0059417 A9 | 3/2011 | Rizoiu et al. |
| 2012/0089134 A1 * | 4/2012 | Horvath et al. .................. 606/6 |
| 2012/0135368 A1 | 5/2012 | Rizoiu et al. |

OTHER PUBLICATIONS

Non-Final Office Action dated Jun. 18, 2013 issued in related/corresponding U.S. Appl. No. 13/630,971, filed Sep. 28, 2012.
International Search Report and Written Opinion dated Feb. 5, 2013 from related/corresponding PCT Patent Application Serial No. PCT/US12/58009, filed Sep. 28, 2012.

* cited by examiner

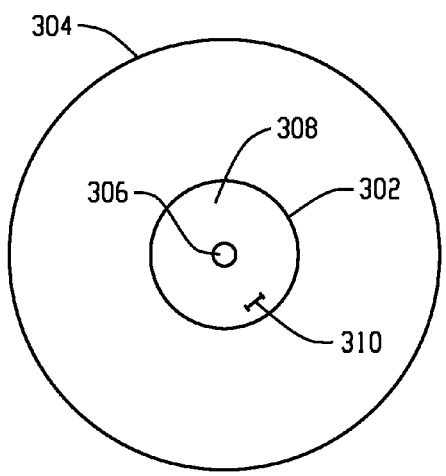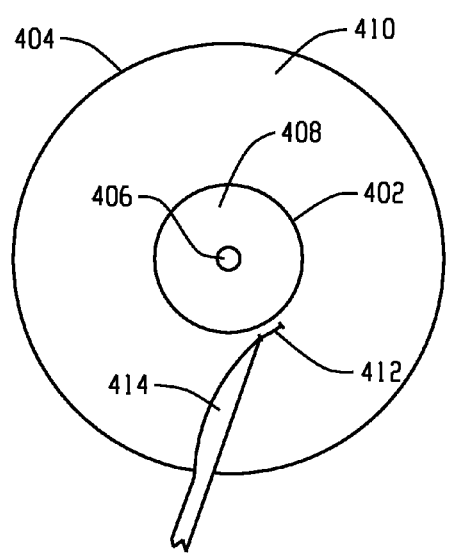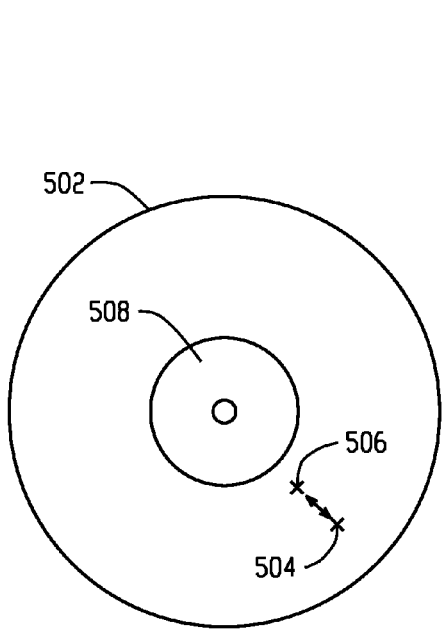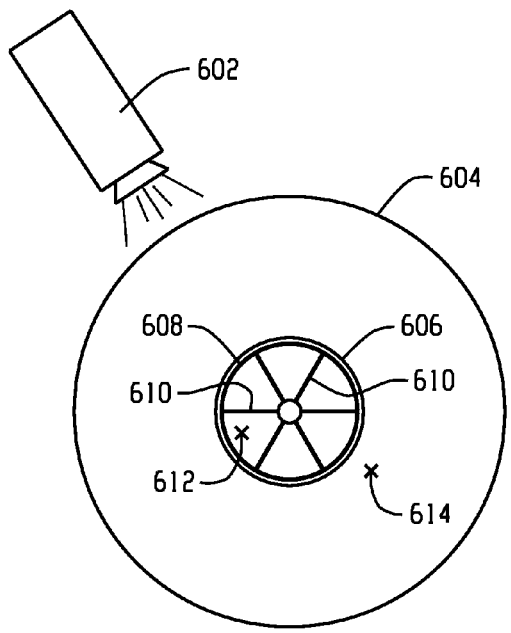
Fig. 3
Fig. 4
Fig. 5
Fig. 6

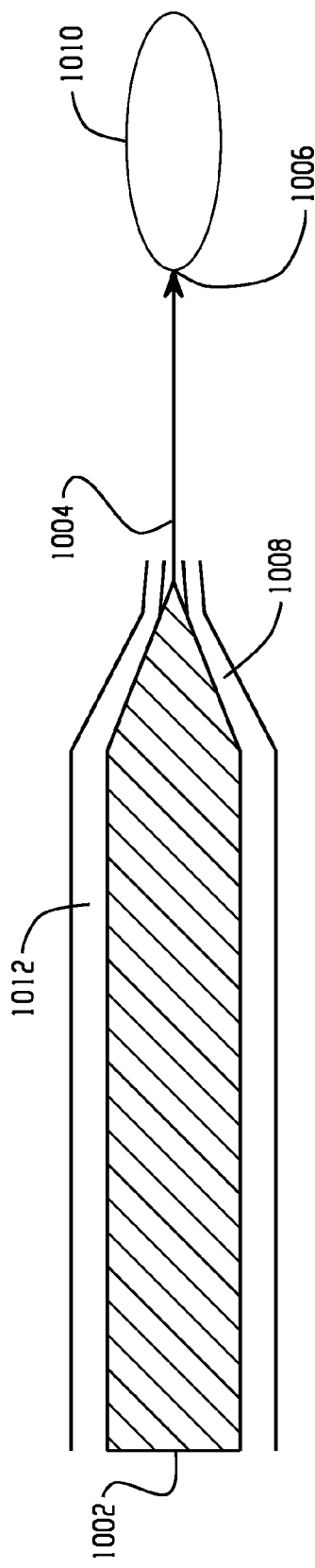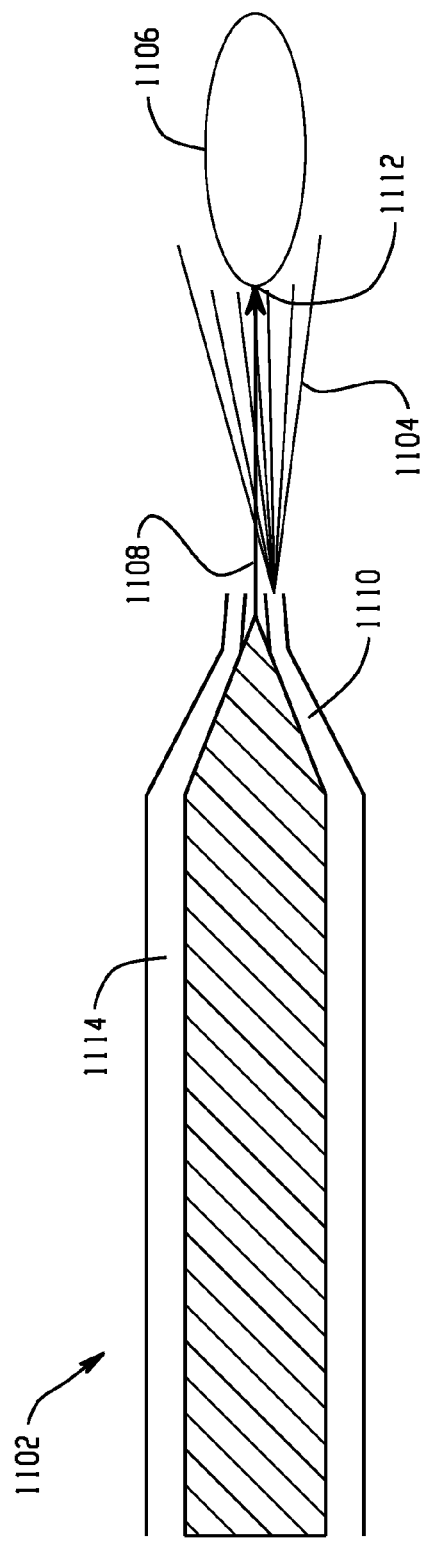

SYSTEMS AND METHODS FOR DISRUPTION OF AN EYE LENS

CROSS-REFERENCE TO RELATED APPLICATIONS

This application claims priority to U.S. Provisional Patent Application No. 61/542,702, filed Oct. 3, 2011, entitled "Lens Disrupting System," and U.S. Provisional Application No. 61/551,826, filed Oct. 26, 2011, entitled "Lens Disrupting System," both of which are herein incorporated by reference in their entirety.

FIELD

The technology described herein relates generally to eye treatment and more particularly eye tissue ablation.

BACKGROUND

A cataract is a clouding that develops in the crystalline lens of the eye or in its envelope (lens capsule), varying in degree from slight to complete opacity and obstructing the passage of light. Cataracts may be partial or complete, stationary or progressive, or hard or soft. Generally, as cataracts progress, the hardness or toughness of the cataract increases. Cataracts are sometimes treated by cutting the affected lens using a scalpel and removing the lens from the eye before replacing the lens. Such treatment can require large incisions to the eye and can put sensitive, non-lens tissue at risk, especially as a cataract hardens and becomes more difficult to cut.

SUMMARY

Examples of systems and methods are provided for ablating a lens of an eye. An access incision is made through outer eye tissue to access the lens. A laser tool is inserted through the access incision. Electromagnetic energy is focused using the inserted laser tool to ablate a portion of the lens, where said ablation breaks the lens into a plurality of pieces for removal from the eye.

In another example, a system for ablating a lens of an eye includes a visible light pattern projector configured to project an ablation pattern onto the lens of the eye. A laser tool is configured to be inserted through an access incision in the eye. The laser tool includes an irrigation port configured to introduce water to the lens via a spray, a flexible tip that is configured to focus electromagnetic energy according to the visible light pattern, where the electromagnetic energy reacts with the water to ablate the lens into a plurality of pieces, and an aspiration port configured to remove the plurality of pieces of the lens via suction following ablation of the lens.

BRIEF DESCRIPTION OF THE DRAWINGS

FIG. 3 depicts a top view of an access incision made from in front of or above of the lens.

FIG. 4 is a diagram depicting access to the lens via an incision through outer eye tissue outside of the radius of the lens.

FIG. 5 depicts a benefit of an incision from outside of the radius of the lens that can be achieved through rotation of the conjunctiva.

FIG. 6 is a diagram depicting a visible light pattern projector that projects an ablation pattern onto the lens of an eye.

FIG. 10 is a diagram depicting an example laser tool.

FIG. 11 is a diagram depicting a potential benefit of water from the irrigation port.

DETAILED DESCRIPTION

Figure 1:
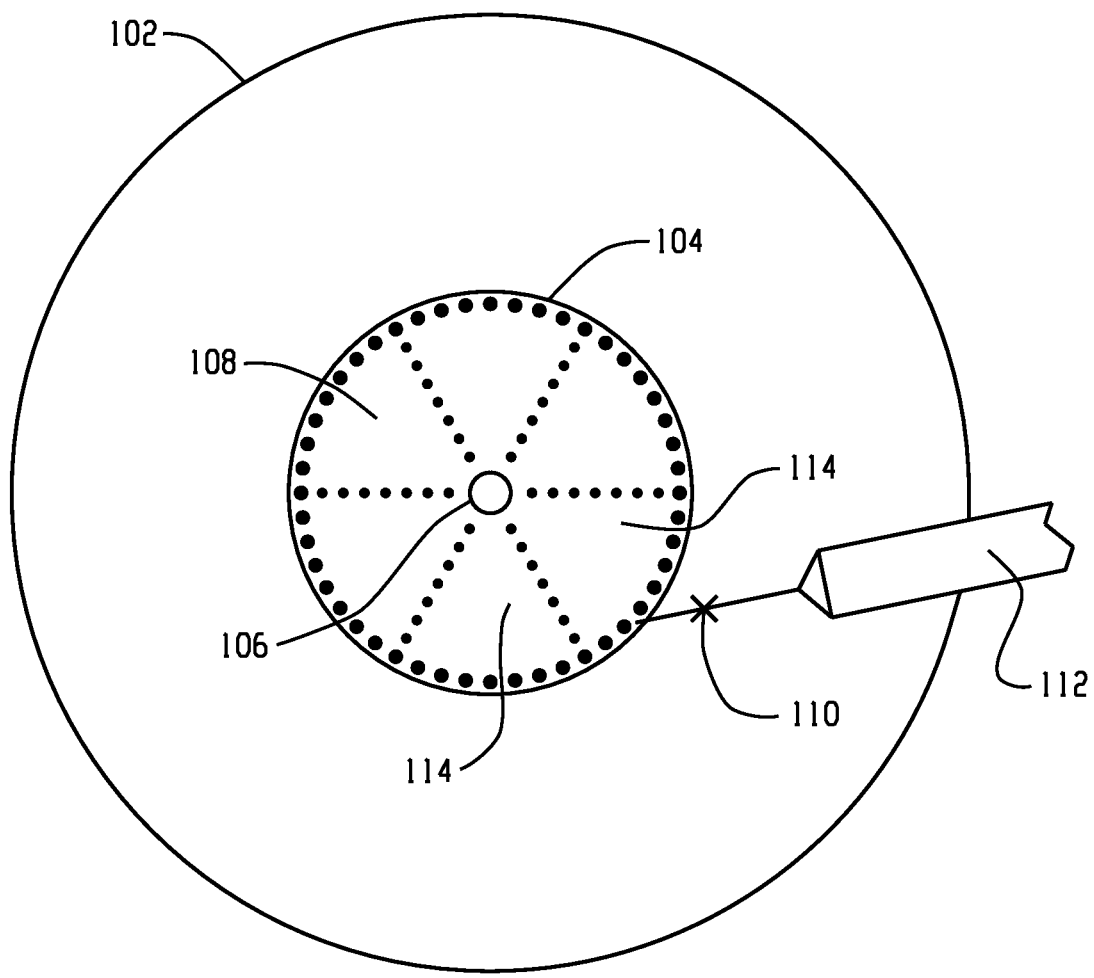
FIG. 1 is diagram depicting the ablating of a lens of an eye.

FIG. 1 is diagram depicting the ablating of a lens of an eye. An eye 102 is depicted, where the eye 102 includes a lens 104 positioned within the eye 102. At least a portion of the lens 104 is visible from the outside of the eye through a pupil 106. A portion of the lens 104 may be hidden from view by an iris 108. During an eye procedure, the pupil may be dilated to provide better access to and vision of the lens 104.

In certain procedures, it is desirable to remove, destroy, or break apart certain tissue within the eye 102. For example, in a cataract treatment procedure, it may be desirable to remove a cataract affected lens and replace the removed lens 104 with a replacement lens (e.g., a synthetic replacement lens). Lens 104 removal may be desirable for treatment of other conditions, such as presbyopia, where the lens 104 becomes unable to change its curvature for near vision.

Large incisions in the eye can affect vision as well as being painful, slow healing, and susceptible to infection. Thus, when performing an eye treatment that requires removal of the lens 104, making an incision that spans the entire width of the lens 104 may be less than optimal. FIG. 1 depicts a method of ablating a lens of an eye for removal that may be able to be performed via a smaller access incision. An access incision 110, identified by an 'x' in FIG. 1, is made through outer eye tissue to access the lens 104. A laser tool 112, or a portion thereof, is inserted through the access incision 110. Electromagnetic energy is focused using the inserted laser tool 112 to ablate a portion of the lens 104, where that ablation breaks the lens into a plurality of pieces for removal from the eye 102. In the example of FIG. 1, the electromagnetic energy is focused along the dotted lines to break the lens into a plurality of pie shape pieces 114. These pie shape pieces 114 are smaller than the entire lens 104 and can be extracted through the access incision 110. The plurality of pieces 114 can be removed in a variety of ways, such as via tweezers or suction.

Figure 2:
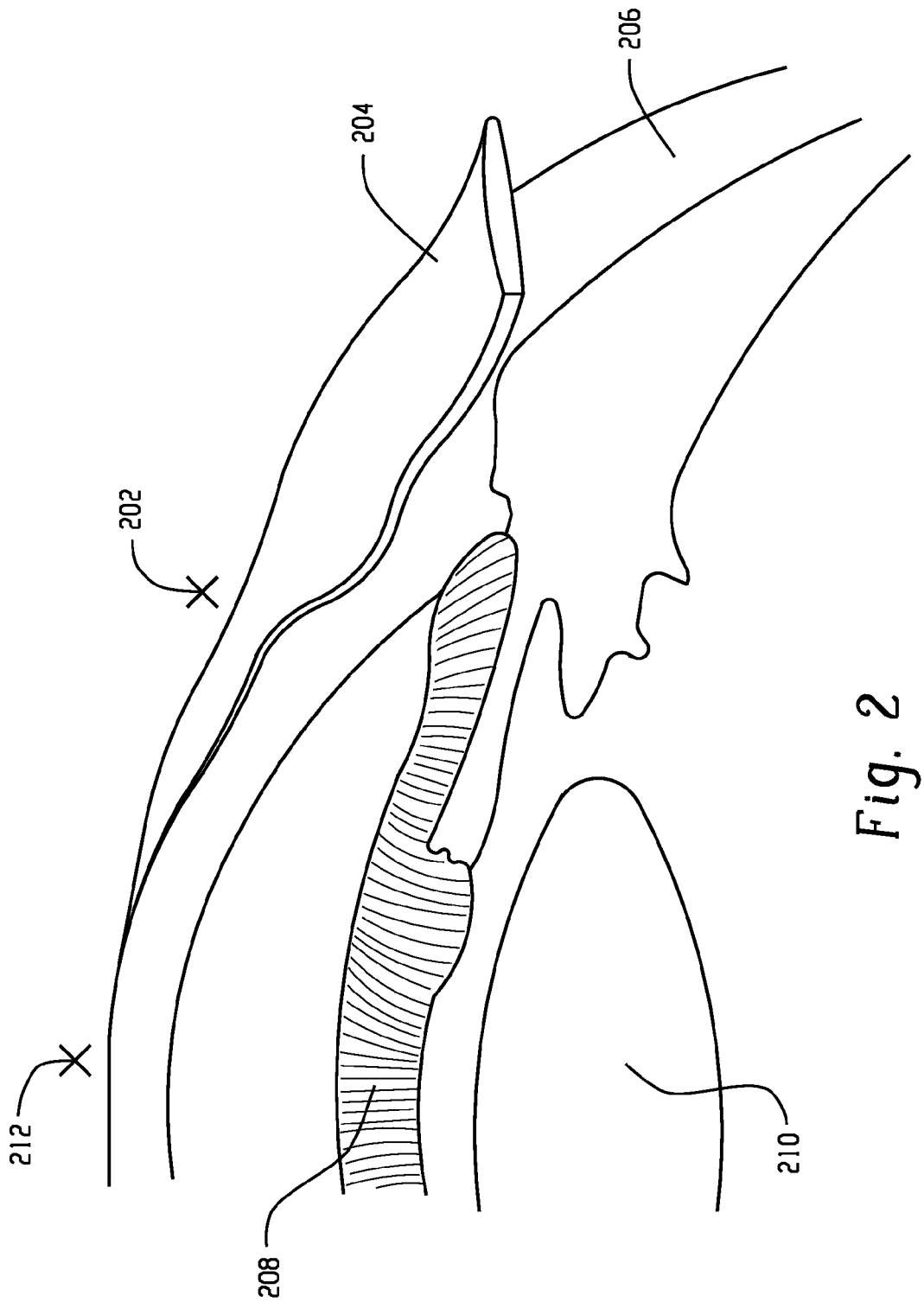
FIG. 2 is a side view of an eye depicting access to interior tissue of the eye via an access incision.
Figure 7A:
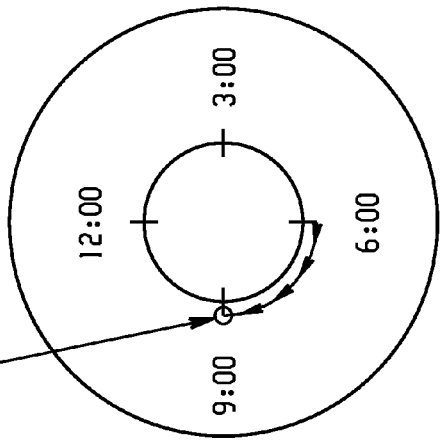
FIG. 7 is a diagram depicting an example ablation of portions of a projected pattern using a flexible laser tip laser tool.
Figure 7B:
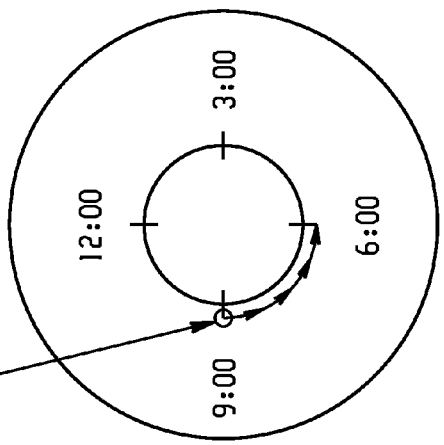
Figure 7C:
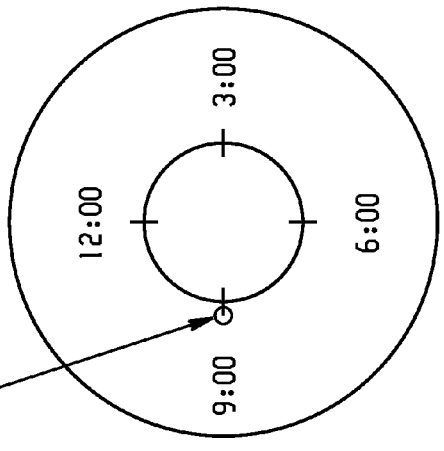
Figure 7E:
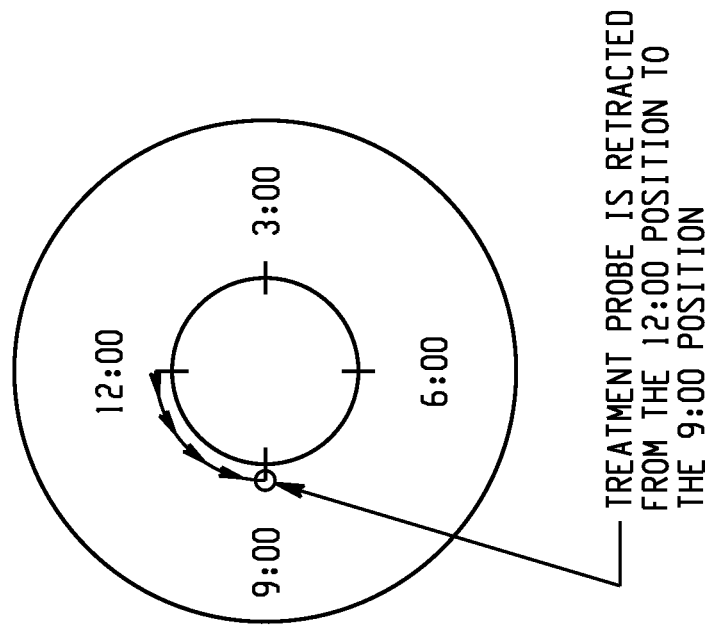
Figure 7D:
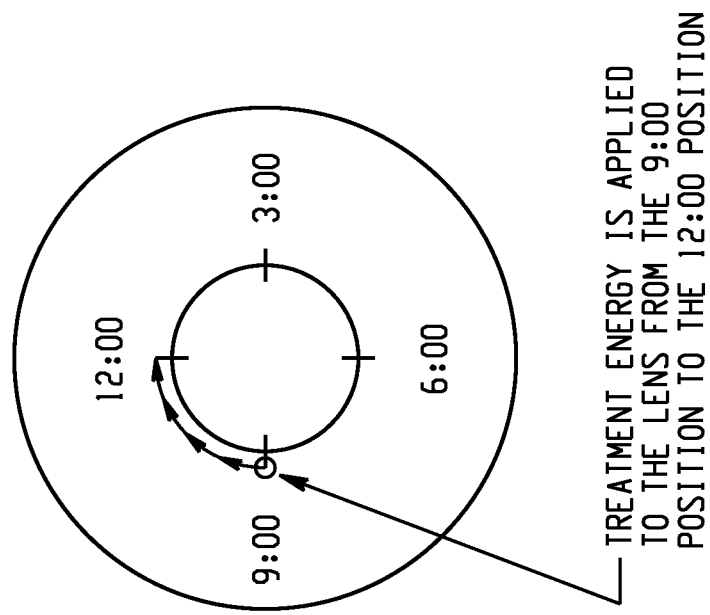

FIG. 2 is a side view of an eye depicting access to interior tissue of the eye via an access incision. An access incision 202 is made through certain layers of outer eye tissue such as the conjunctiva 204 and the sclera 206. The access incision 202 may also traverse certain internal eye structure, such as the trabecular meshwork 208, in seeking access to internal structure, such as the lens 210. In a lens extracting procedure, the lens 210 or tissue surrounding the lens 210 is accessed via the access incision 202 for extraction. Electromagnetic energy is focused through the access incision 202 on the lens 210 or tissue surrounding the lens 210 to detach the lens 210 from the eye and break apart the lens for extraction through the access incision 202. In one example, a laser tool (e.g., a flexible laser tip) is inserted through the access incision 202 and maneuvered to focus electromagnetic energy on the lens 210 to ablate the lens 210 into a plurality of pieces for extraction according to a predetermined pattern.

While FIG. 2 depicts access to the lens via an access incision 202 made from outside of the radius of the lens 210, the lens 210 and other internal structures can be accessed via other types of access incisions, such as an access incision made from in front of or above the lens, as indicated at 212 as well as other types of incisions. FIG. 3 depicts a top view of such an access incision from in front of or above the lens. In FIG. 3, a lens 302 is depicted at the center of an eye 304, where the lens 302 is visible through a pupil 306 at the center of an iris 308. During a procedure, the pupil 306 may be dilated, and the access incision 310 may be made in front of or on top of the lens 302 to access the lens 302 through the pupil 306.

FIG. 4 is a diagram depicting access to the lens via an incision through outer eye tissue outside of the radius of the lens. In FIG. 4, a lens 402 is depicted at the center of an eye 404. The lens 402 is visible through the pupil of the eye 406 that is surrounded by the iris 408. The iris 408 is surrounded by certain outer layers of eye tissue, such as the sclera and conjunctiva, the white portion of the eye. In the example of FIG. 4, the lens is accessed via an access incision 412 (e.g., a 3 mm incision) made through the outer eye tissue 410 near, but outside, of the radius of the lens 402 (e.g., through the corneascleral rim). The incision 412 may be made using a cutting tool, such as a scalpel or a laser. The same cutting tool 414 or another cutting tool of the same or differing type is inserted through the access incision 412 to access the inner eye tissue, such as the lens 402. For example, a laser tool, such as a flexible or inflexible tip, may be used to make the access incision 412, where the laser tool is inserted through the access incision 412 to focus electromagnetic energy on the lens 402 to ablate the lens into a plurality of pieces to ease removal of the lens from the eye 404. The laser tool (e.g., a mid-infrared laser with a wavelength between 2,750 and 3,000 nm) may be operated at different settings based on the type of tissue that is being cut or ablated (e.g., energy levels from 0.05 to 3 Watts at 5-100 Hz). For example, a setting of 1.25 Watts at 20 Hz and short pulse duration may be used for cutting through the conjunctiva, while a 0.25 Watts at 30 Hz setting may be used for lens ablation, with higher settings (e.g., 0.75 Watts) being utilized for harder cataracts.

Ablations may be made using a number of mechanisms. For example, ablations may be made using a hand-laser tool maneuvered by a surgeon or other technician performing an ablation treatment. In another example, ablations may be made using a computer-controlled scanner that is configured to make ablations at one or more points at a time in the process of making a pattern of ablations according to a pre-defined or pre-programmed pattern. Such ablation procedures can enable division of the lens into a plurality of pieces for extraction without use of ultrasonic or other shaking procedures, which can damage eye tissue.

Making the access incision outside of the radius can have a number of advantages. For example, an access incision made outside of the radius of the lens can avoid unintended damage to certain sensitive eye structures when performing treatments. For instance, when accessing a lens from the front or above the lens through the pupil, the integrity of the pupil is jeopardized by potential damage to the iris. By accessing the lens from the side, such risks can be mitigated.

FIG. 5 depicts another potential benefit of an incision from outside of the radius of the lens that can be achieved through rotation of the conjunctiva. The conjunctiva and the sclera 502 are outer layers of eye tissue that form the white part of an eye, where the conjunctiva sits on top of the sclera and can be slid or rotated relative to the sclera. In the example of FIG. 5, the conjunctiva layer is rotated from a rested position 504 to a rotated position 506 relative to the sclera and other underlying eye tissue, such as the lens 508. The conjunctiva may be held in the rotated position 506 using a finger or clamp. The access incision at 506 is made near the outside of the lens at 506 with the conjunctiva in the rotated position 506. The access incision traverses the conjunctiva and sclera to access inner eye tissue, such as the lens 508. The conjunctiva is kept in the rotated position 506 and treatments are applied to the inner eye tissue through the access incision that breaches the conjunctiva at the rotated position indicated at 506 and other eye tissue below that point.

When the treatment is completed and treatment tools are removed from the access incision, the conjunctiva is allowed to return to its rested position 504. As the conjunctiva relaxes to its relaxed position 504, the part of the access incision that is through the conjunctiva moves to the rested position 504, while the part of the access incision that is through the lower layers of eye tissue, such as the sclera, remains near the lens 508. In this way, the damaged portions of the conjunctiva and the sclera and other internal eye tissue are staggered. This staggering provides an undamaged portion of conjunctiva to cover the damaged sclera and lower level tissue, which can help in preventing infection. Further, the staggering of the damaged layers of eye tissue improves blood flow to the individually damaged layers, improving healing times.

In certain implementations, it may be desirable to ablate target eye tissue according to a predetermined or predefined pattern. For example, during a procedure to remove a lens of an eye, the lens may be ablated into a plurality of pieces according to a pattern for removal through an incision that is smaller than the full diameter of the lens. FIG. 6 is a diagram depicting a visible light pattern projector that projects an ablation pattern onto the lens of an eye. A visible light pattern projector 602 projects a pattern of visible light onto a portion of an eye 604. In the example of FIG. 6, the visible light pattern projector 602 transmits a pattern onto the lens 606 of the eye 604, identifying a pattern to be followed in cutting the lens 606 using a scalpel, laser, or other cutting tool for extraction of the lens 606 from the eye 604. The pattern in FIG. 6 is a pie shaped pattern consisting of a substantially circular first portion 608 and a second part 610 that consists of a plurality of cross-cuts within the substantially circular first portion 608. The visible light pattern may be projected using a variety of mechanisms, such as a low power laser or visible light projected through a mask. The visible light pattern may be projected in a variety of ways, including in three dimensions (3D). For example, a 3D pattern may be utilized to help guide the depth of certain ablations or cuts.

Access to the lens 606 is achieved through an access incision which may be made from in front of or above the lens 606, as indicated at 612 or from outside of the radius of the lens 606, as indicated at 614. Upon accessing the lens 606, the lens 606 is divided into a plurality of pieces by making cuts or ablations along or through the lines of the pattern 608, 610 projected onto the lens 606 by the visible light pattern projector 602. For example, electromagnetic energy may be focused through a flexible laser tip inserted at access incision 614 to ablate the lens 606 along the substantially circular first part 608 of the projected pattern and then along the internal cross-cuts of the second part 610 of the visible light pattern 608, 610. In another example, the internal cross-cuts of the second part 610 may be made before making the substantially circular cuts of the first part 608 of the pattern. The individual pieces of the lens 606 remaining after the laser ablation may then be removed from the eye 604 through the access incision 614 allowing minimization of the size of the access incision 614 needed for removal of the lens 606.

FIG. 7 is a diagram depicting an example ablation of portions of a projected pattern using a flexible laser tip laser tool. In FIG. 7a, the flexible tip is inserted through an access incision near the 9:00 position of the lens. In FIG. 7b, electromagnetic energy is focused along the periphery of the lens from the 9:00 position toward the 6:00 position, ablating the outside edge of the lens, such as according to a substantially circular portion of an ablation pattern projected onto the lens. In some implementations, the electromagnetic energy may be focused all of the way to the 3:00 position through maneuvering of the flexible laser tip. In FIG. 7c, the flexible tip is retracted to the 9:00 position, and in FIG. 7d, electromagnetic energy is focused in the other direction along the edge of the lens through the 12:00 position and continuing to the 3:00 position to complete the ablation of the outside edge of the lens. In FIG. 7e, the flexible laser tip is retracted to the 9:00 position and removed through the access incision.

Figure 8:
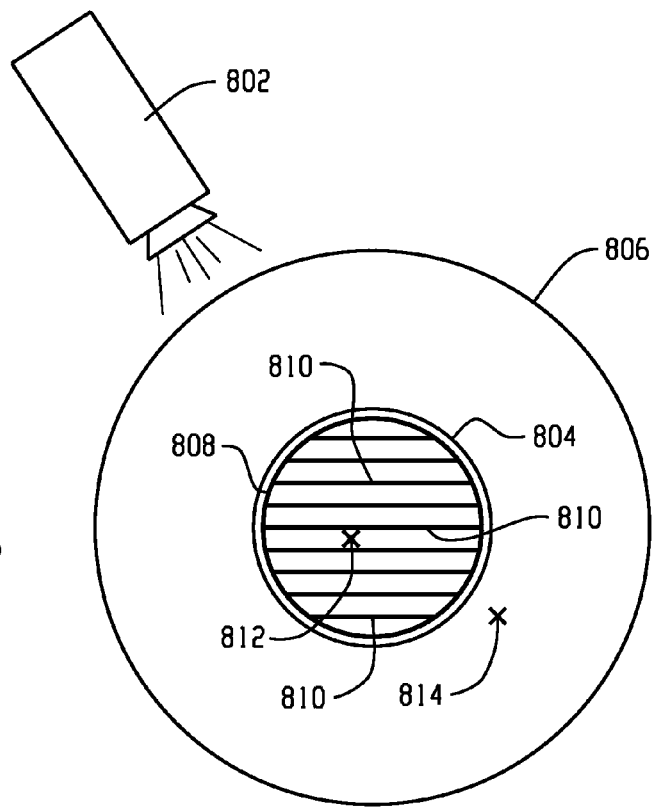
FIG. 8 is a diagram depicting a visible light pattern projector projecting a thin-slice pattern onto an eye lens.

Patterns projected by a visible light pattern projector may take a variety of forms. FIG. 8 is a diagram depicting a visible light pattern projector projecting a thin-slice pattern onto an eye lens. The visible light pattern projector 802 projects a visible light pattern onto a lens 804 of an eye 806, such as for guiding cutting or ablation of the eye lens tissue 804. The pattern projected in FIG. 8 consists of a first, substantially circular part 808 and a plurality of parallel cross-cuts 810. In practice, a cutting tool may be inserted through an access incision, such as one of the incisions depicted at 812, 814. The cutting tool may be used to cut or ablate the lens 804 along the plurality of parallel cross-cut lines 810 that are projected onto the lens 804 by the visible light pattern projector 802. The cutting tool may then be used to cut or ablate the lens 804 along the substantially circular 808 part of the projected pattern. It is noted that the order of the cuts along or through the projected pattern may be changed. The plurality of resulting strips of the lens can then be extracted through the utilized access incision 812, 814.

Figure 9:
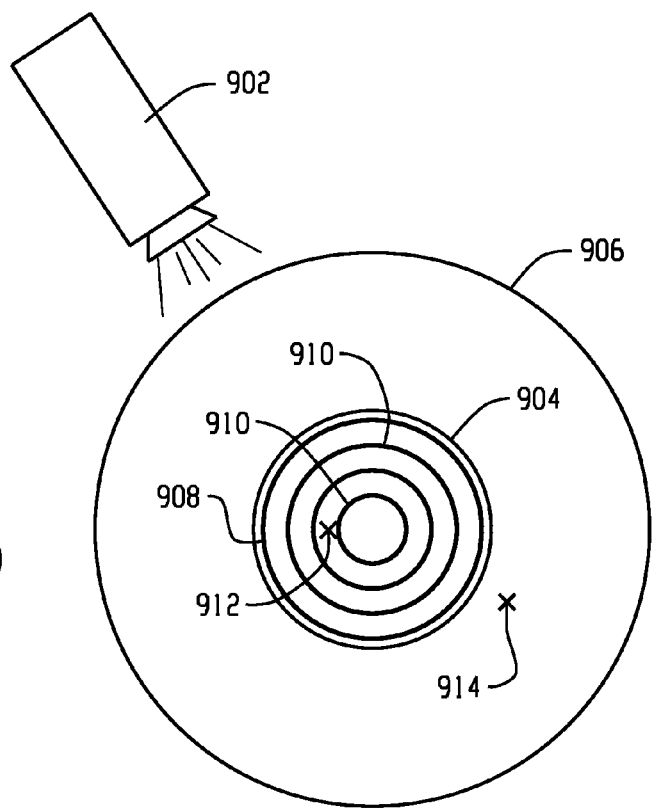
FIG. 9 is a diagram depicting a visible light pattern projector projecting a concentric circle pattern onto an eye lens.

FIG. 9 is a diagram depicting a visible light pattern projector projecting a concentric circle pattern onto an eye lens. The visible light pattern projector 902 projects a visible light pattern onto a lens 904 of an eye 906, such as for guiding cutting or ablation of the eye lens tissue 904. The pattern projected in FIG. 9 consists of a first, substantially circular part 908 and a plurality of concentric circle inner cuts 910. In practice, a cutting tool may be inserted through an access incision, such as one of the incisions depicted at 912, 914. The cutting tool may be used to cut, ablate, or disrupt the lens 904 along the plurality of concentric circle lines 910 that are projected onto the lens 904 by the visible light pattern projector 902 or using a computer scanner with an optical system such as LensX. The cutting tool may then be used to cut or ablate the lens 904 along the substantially circular 908 part of the projected pattern. The plurality of resulting strips of the lens can then be extracted through the utilized access incision 912, 914 (e.g., an arcuit excimer incision), such as by folding the circular portions of the lens prior to removal, where such folding of a solid, uncut lens is not possible.

FIG. 10 is a diagram depicting an example laser tool. Electromagnetic energy, such as laser energy, is provided to the laser tool at a first end 1002. The electromagnetic energy is propagated along the length of the laser tool, through a laser tip 1004, where the electromagnetic energy is radiated from at least the end 1006 of the laser tip 1004. The laser tool depicted in FIG. 10 may further include an irrigation port 1008 that is configured to introduce water to a treatment site, such as a lens 1010 of an eye, by spraying water from the irrigation port 1008 to the treatment site near the end 1006 of the laser tip 1004. The water provided by the irrigation port 1008 may serve a variety of purposes. For example, the irrigation port may provide water to a lens 1010 treatment site to loosen fragments of the lens 1010 to ease extraction of the fragments via suction from an aspiration port 1012

FIG. 11 is a diagram depicting an additional potential benefit of water from the irrigation port. In the example of FIG. 11, the electromagnetic energy is provided by a 2.78 nm Er:YSGG laser. The effectiveness of such a laser 1102 in performing ablation and cutting treatments is enhanced when that laser 1102 interacts with water 1104 present at the treatment site, such as the lens treatment site 1106. In fact, such a laser 1102 may not perform any cutting or ablating when its electromagnetic energy 1108 is focused outside of the presence of water 1104. However, when such a laser 1102 is focused at a treatment site 1106 where water 1104 is present, such as water 1104 sprayed from the irrigation port 1110, tissue at the treatment site, such as the lens 1106 is cut or ablated (e.g., via micro-expansion and micro-ablation of the water), as indicated at 1112. One such laser is described in U.S. Pat. No. 8,033,825, the entirety of which is herein incorporated by reference. Following ablation using water from the irrigation port 1110, the plurality of pieces of the lens 1106 may be extracted via the aspiration port 1114 with or without additional water 1104 from the irrigation port 1110 as an aid.

Figure 12:
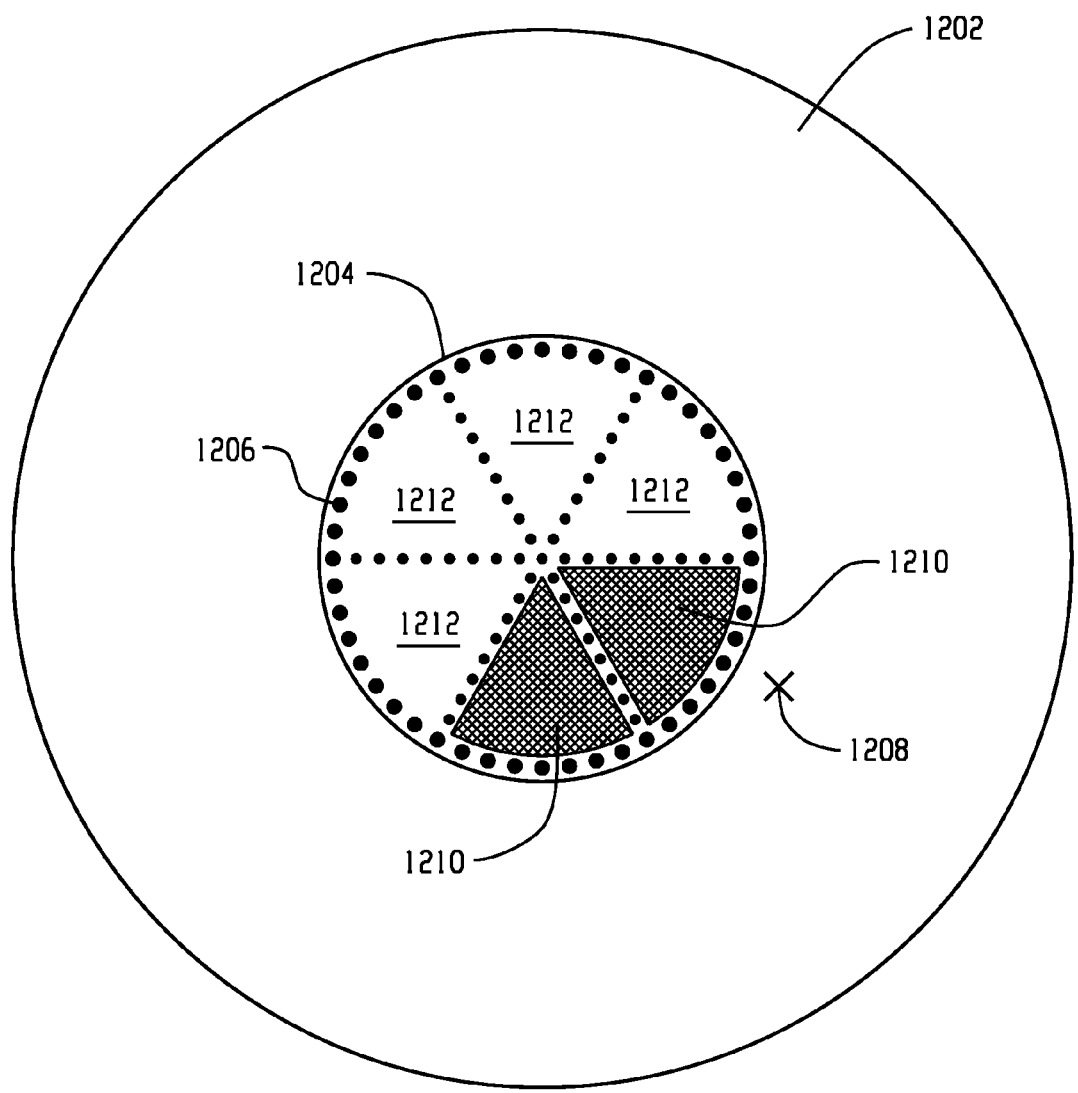
FIG. 12 is a diagram depicting removal of certain pieces of an ablated lens.

Following ablation of portions of the lens to divide the lens into a plurality of pieces, the pieces of the lens are removed from the eye, such as via the aspiration port depicted in FIGS. 10 and 11, using surgical tweezers, or otherwise. FIG. 12 is a diagram depicting removal of certain pieces of an ablated lens. The depicted eye 1202 includes a lens 1204, which has been ablated in a pie shaped pattern 1206. The dotted lines represent lens tissue that has been ablated and is no longer present as part of the lens pieces. Following the ablation, the lens 1204 is divided into six pie shaped pieces. Each of these pieces is smaller than the lens 1204 as a whole and can thus be removed through a smaller incision, such as the incision depicted at 1208. Each of the pieces is removed in separately. In the example of FIG. 12, two of the pieces 1210 have been removed, while four of the pie shaped pieces 1212 have yet to be removed through the access incision 1206.

Figure 13:
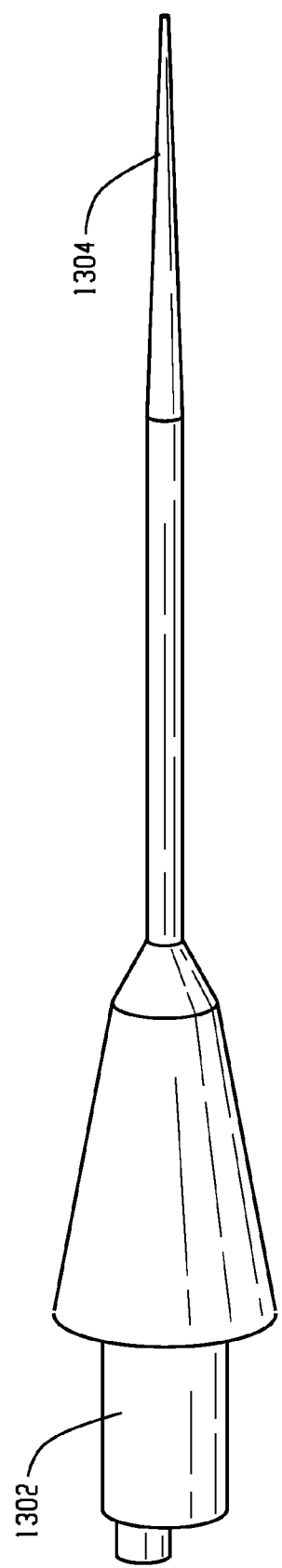
FIG. 13 depicts an example laser tool that includes a flexible tip.
Figure 17C:
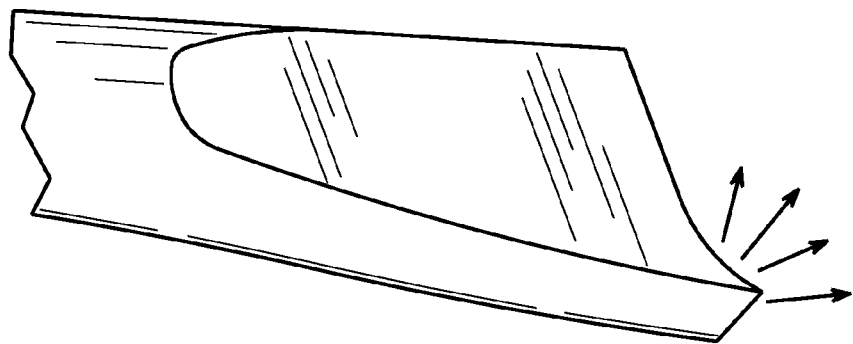
FIG. 17 depicts exemplary laser tips.
Figure 17B:
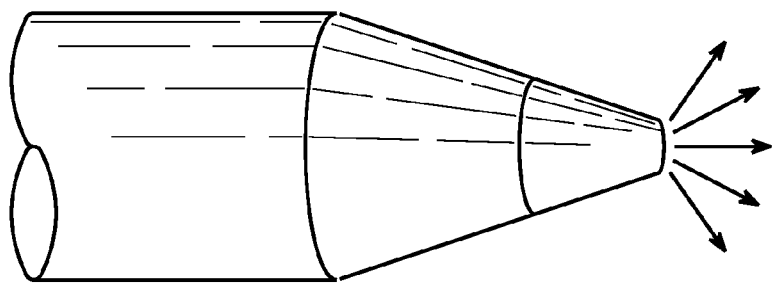
Figure 17A:
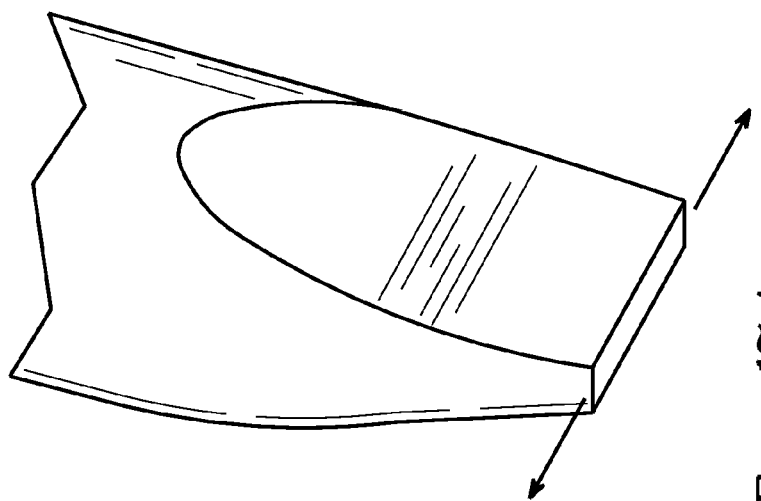

As noted above, lens and other eye tissue ablations can be performed using a variety of different laser tips of varying types and sizes. FIG. 13 depicts an example laser tool that includes a flexible tip. The laser tool may utilize a LensSx® Laser from Alcon Laboratories, Inc., an excimer laser, or other type of laser. A flexible tip 1304 enables ablation of portions of a lens or other tissue in an eye. The flexible tip 1304 may take a variety of forms, such as an end-firing flat, pointed, or curved tip or a side firing tip or radial firing tip. The laser tip 1304 may take a variety of forms. For example, the laser tip 1304 may be a side firing laser tip, such as those disclosed in U.S. Pat. No. 8,221,117 or U.S. Pat. No. 7,702,196, the entirety of both of which is herein incorporated by reference. Certain example laser tips are depicting in FIG. 17. Example laser tips 1304 can further include the Perio 300 tip by BioLase, Inc., Part Number 740020. This tip has Twist-on convenience and eliminates time-consuming stripping and cleaving. This tip is bendable for access to all areas of the eye and can be used as a single use tip. The Perio 300 tip has a diameter of 1.1 mm and a fiber length of 7 mm or 9 mm with an outer tube length of 15 mm.

Figure 14:
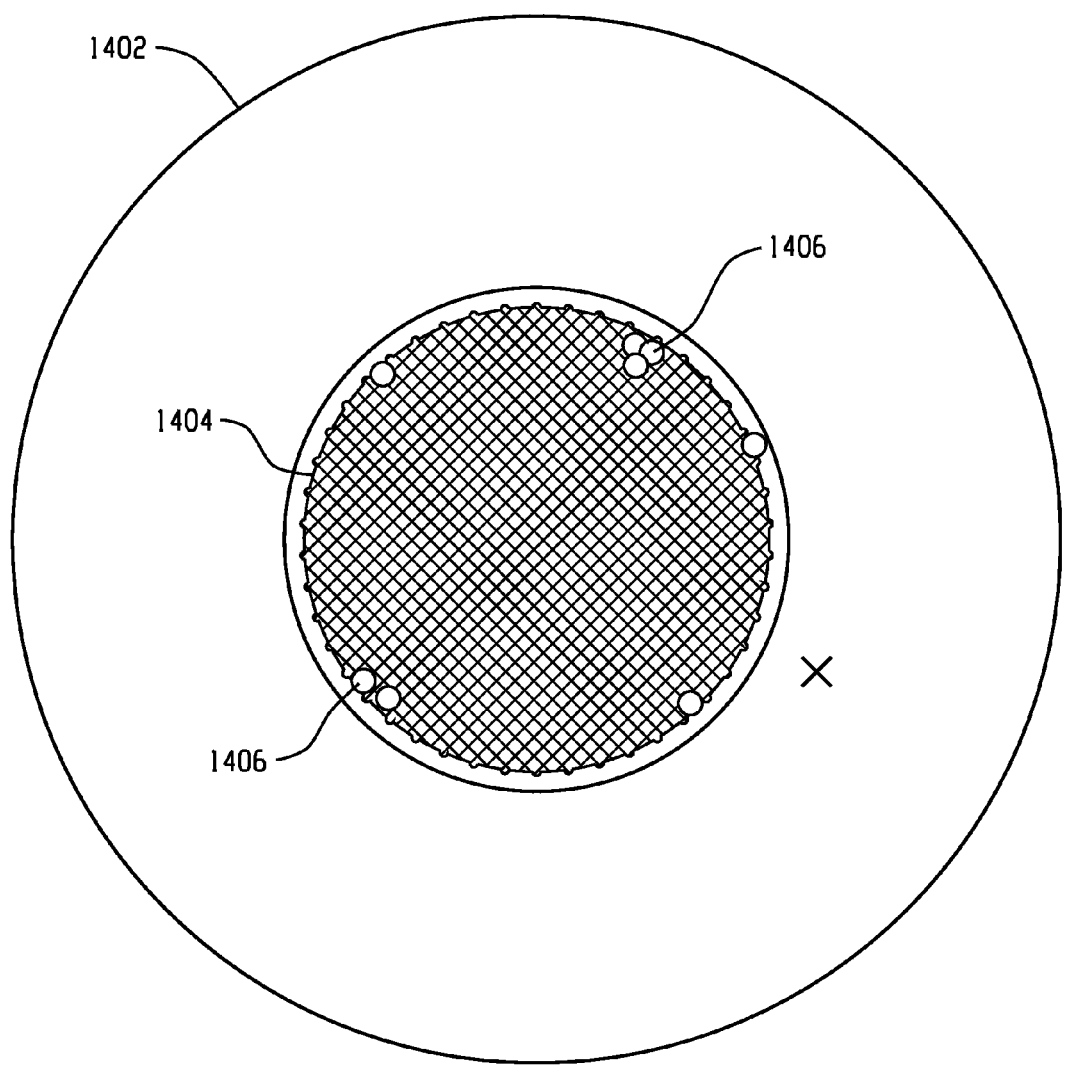
FIG. 14 is a diagram depicting an eye with a removed lens having germination cells present.

Following removal or all or most of the lens of an eye, certain undesirable remnants of the lens or other unwanted tissue may remain in the eye. For example, during a cataract removal procedure, germination cells may remain in the eye following ablation of the lens. Over time, these germination cells can be a starting point for the generation of a new cataract on a replacement lens, limiting the benefit of the cataract procedure. Thus, it may be desirable to locate and ablate any germination cells after lens removal and prior to the end of a procedure. Germination cells can be seen using a microscope or the naked eye following removal of the lens. FIG. 14 is a diagram depicting an eye with a removed lens having germination cells present. FIG. 14 depicts an eye 1402 having a lens 1404 that has been removed, such as using one of the procedures described above. Follow removal of the lens 1404, germination cells 1406 reside at or near the site of the removed lens. To prevent cataract regrowth, these germination cells 1406 are located, and electromagnetic energy is focused on the germination cells 1406 to ablate the germination cells 1406.

Figure 15:
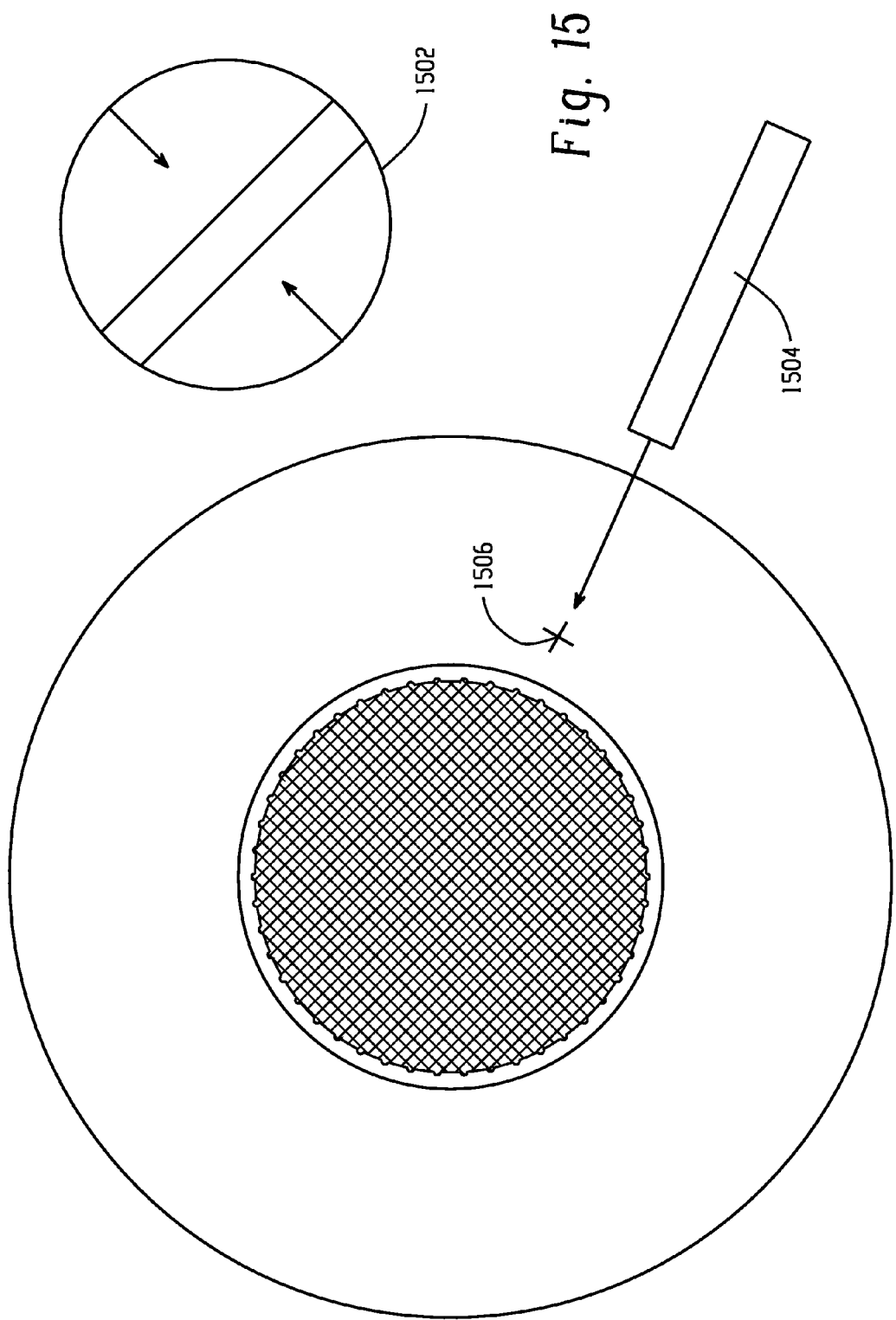
FIG. 15 is a diagram depicting insertion of a replacement lens using a folded lens technique.
Figure 16:
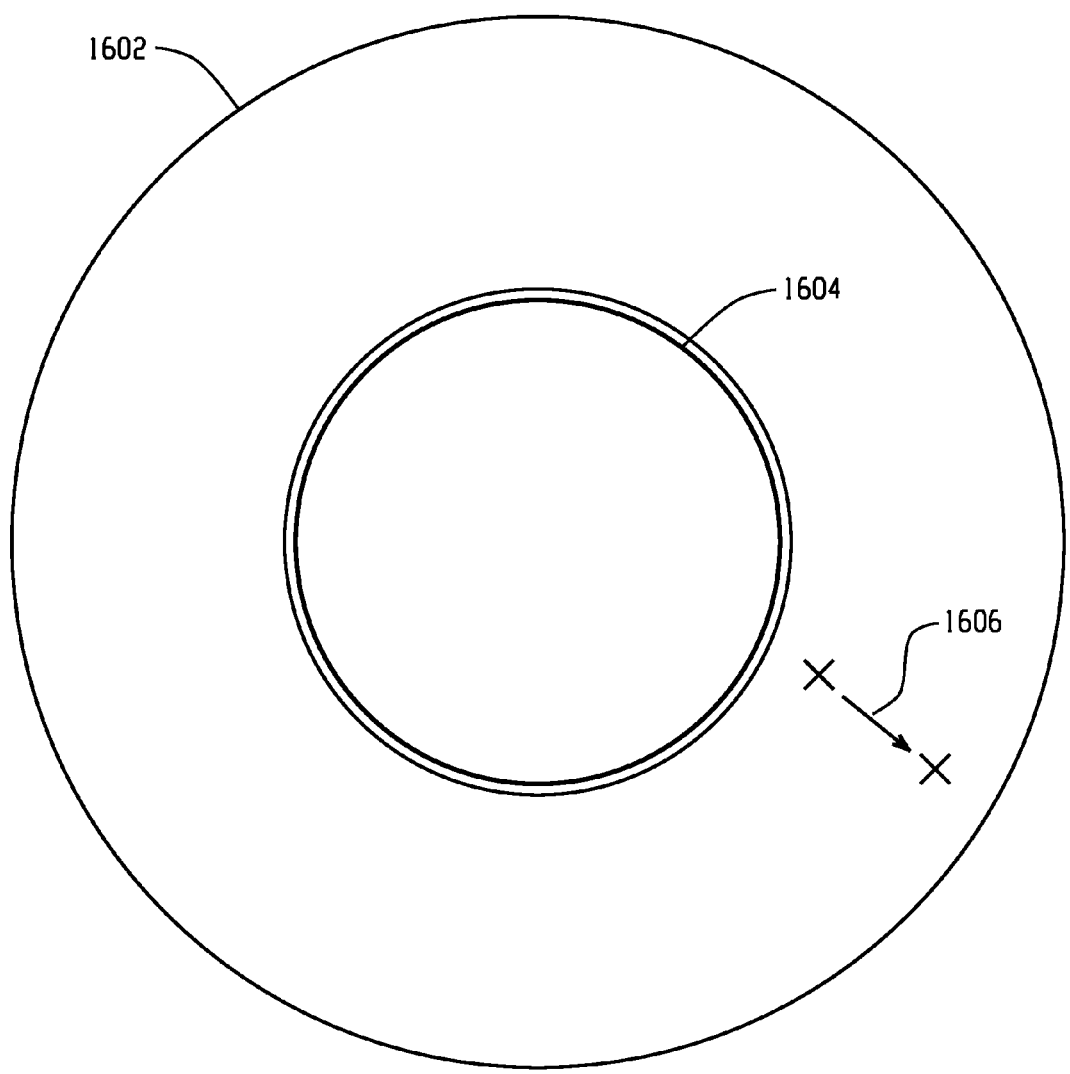
FIG. 16 is a diagram depicting an eye having a replacement lens positioned following removal of a prior lens.

Following removal of the lens of an eye, a replacement intraocular lens may be positioned within the capsular bag that the natural lens previously occupied. FIG. 15 is a diagram depicting insertion of a replacement lens using a folded lens technique. A lens in an unfolded shape is depicted at 1502. That unfolded lens 1502 may be folded one or more times as indicated, to reduce the width of the folded lens 1504 to a width that can fit through an access incision 1506. During a procedure, the folded lens 1504 is inserted into the membrane pocket that the natural lens previously occupied. Once inside the eye, the lens is unfolded and positioned correctly. FIG. 16 is a diagram depicting an eye having a replacement lens positioned following removal of a prior lens. The eye 1602 includes a replacement lens 1604, indicated by the thick line, which has been positioned in the place of a natural or previously positioned lens. Following, completion of the procedure, if the conjunctiva was rotated prior to making the access incision, that rotation can be released, moving the conjunctiva incision away from the procedure site, as indicated at 1606, which provides potential improvement in the healing of both the conjunctiva and the underlying procedure site.

This application uses examples to illustrate the invention. The patentable scope of the invention may include other examples.

What is claimed is:

1. A method of ablating a lens of an eye, comprising:
projecting, onto the lens of the eye, a visible light pattern that follows a circumferential path along a periphery of the lens;
making an access incision through outer eye tissue to access the lens;
inserting a tip of a laser hand tool through the access incision,
the laser hand tool including an irrigation port configured to introduce water through the tip to a lens treatment site using a spray;
maneuvering, by a user, the tip along the circumferential path defined by the visible light pattern, the maneuvering occurring while the tip remains inserted through the access incision and ablates the lens along the circumferential path and while the user is viewing the visible light pattern and uses the visible light pattern as a guide for maneuvering the tip; and
wherein the introduced water loosens fragments of the lens; and
removing the lens from the eye.

2. The method of claim 1, wherein a first part of the ablation pattern is circular in shape, and wherein the first part is projected on or near an outside edge of the lens to detach the lens from the eye.

3. The method of claim 2, wherein a second part of the ablation pattern is within the circular first part, and wherein the electromagnetic energy is focused through the second part of the ablation pattern to ablate the lens into a plurality of pieces.

4. The method of claim 1, further comprising:
removing the plurality of pieces through the access incision.

5. The method of claim 1, wherein the lens is too big for removal through the access incision prior to ablation into the plurality of pieces.

6. The method of claim 1, wherein the access incision is an incision made through outer eye tissue in front of or above the lens.

7. The method of claim 1, wherein the access incision is an incision made through a conjunctiva of the eye outside of a radius of the lens.

8. The method of claim 1, further comprising:
rotating the conjunctiva from a rested position to a rotated position prior to making the access incision; and
releasing the conjunctiva from the rotated position to the rested position following ablation of the lens, wherein when the conjunctiva is in the rested position, the access incision is further from the lens than when the conjunctiva is in the rotated position.

9. The method of claim 1, wherein the tip is a flexible laser tip that projects outward from the tool.

10. The method of claim 9, wherein the flexible laser tip is a side-firing laser tip or a radial-firing laser tip.

11. The method of claim 1, wherein the electromagnetic energy is focused using a computer-implemented scanner.

12. The method of claim 1, wherein the method further comprises:
focusing the ablating electromagnetic energy on portions of the lens where the sprayed water is present, wherein the laser will not ablate when focused outside the presence of water, but will ablate when focused where water is present, such that the focused electromagnetic energy does not ablate the lens prior to the introduction of water to the lens.

13. The method of claim 1, wherein the lens is ablated without ultrasonic shaking or other shaking.

14. The method claim 1, wherein the laser tool further includes an aspiration port, wherein the method further comprises:
activating the aspiration port to remove the plurality of pieces of the lens via suction following ablation of the lens.

15. The method of claim 1, further comprising:
focusing electromagnetic energy on germination cells that remain in the eye following the ablation of the lens to ablate the germination cells.

16. The method of claim 1, wherein the lens is removed as part of a cataract treatment procedure, wherein the method further includes:
inserting a folded replacement lens into the eye through the access incision, wherein the replacement lens is unfolded in the eye following insertion.

17. The method of claim 1 wherein the maneuvering includes the tip following the lens periphery along at least 90 degrees of the periphery while remaining inserted through the access incision.

18. The method of claim 17 wherein the maneuvering includes the tip following the lens periphery along at least 180 degrees of the periphery while remaining inserted through the access incision.

19. A method of ablating a lens of an eye, comprising:
projecting, onto the lens of the eye, a visible light pattern that follows a path along the lens;
making an access incision through outer eye tissue to access the lens;
inserting a tip of a laser hand tool through the access incision,
the laser hand tool including an irrigation port configured to introduce water through the tip to a lens treatment site using a spray;
maneuvering, by a user, the tip along the path defined by the visible light pattern, the maneuvering occurring while the tip remains inserted through the access incision and ablates the lens along the path within the eye and while the user is viewing the visible light pattern and uses the visible light pattern as a guide for maneuvering the tip; and
wherein the introduced water loosens fragments of the lens.

20. The method of claim 19 further comprising:
removing the lens from the eye.

* * * * *